United States Patent [19]

Bennett et al.

[11] Patent Number: 4,670,609
[45] Date of Patent: Jun. 2, 1987

[54] DIHYDRIC PHENOL RECOVERY PROCESS

[75] Inventors: Ronald Q. Bennett, Wadsworth; Donald E. Smith, Tallmadge; Joel Muse, Jr., Kent, all of Ohio

[73] Assignee: The Goodyear Tire & Rubber Company, Akron, Ohio

[21] Appl. No.: 427,972

[22] Filed: Sep. 29, 1982

[51] Int. Cl.$^4$ .......................................... C07C 37/08
[52] U.S. Cl. ................................... 568/768; 568/570; 568/576; 568/771
[58] Field of Search ............... 568/570, 768, 569, 771, 568/576

[56] References Cited

U.S. PATENT DOCUMENTS

| 3,882,600 | 5/1975 | Miller | 568/768 |
| 3,923,908 | 12/1975 | Suda et al. | 568/768 |
| 3,968,171 | 7/1976 | Burkholder | 568/753 |
| 3,978,142 | 8/1976 | Burkholder | 568/569 |
| 4,049,723 | 9/1977 | Tanaka et al. | 568/753 |
| 4,053,520 | 10/1977 | Miller | 568/569 |
| 4,271,321 | 6/1981 | Voges | 568/569 |

FOREIGN PATENT DOCUMENTS

| 893634 | 4/1962 | United Kingdom | 568/569 |
| 910735 | 11/1962 | United Kingdom | 568/768 |
| 1034896 | 7/1966 | United Kingdom | 568/768 |

OTHER PUBLICATIONS

"Process for the Production of Hydroquinone", by J. Ewers, H. W. Voge and G. Maleck, Erdoel Kohle Erdgas, Petrochem. Br. Chem., vol. 28, No. 1, 1975, pp. 34+.

Primary Examiner—Werren B. Lone
Attorney, Agent, or Firm—Alvin T. Rockhill; C. James Bushman

[57] ABSTRACT

An improved process for the manufacture of a dihydric phenol such as hydroquinone wherein a dialkylbenzene is oxidized to a dihydroperoxide, the dihydroperoxide being extracted from the oxidate by a caustic solution, leaving an organic phase for recycle to the oxidizer, the improvement comprising decreasing the caustic concentration in the recycle organic phase and increasing the dihydroperoxide concentration of the recycle phase by washing the organic phase from the caustic extract with an aqueous phase removed from the oxidizer, separating the organic phase from the aqueous phase and subsequently introducing the organic phase to the oxidizer.

7 Claims, 1 Drawing Figure

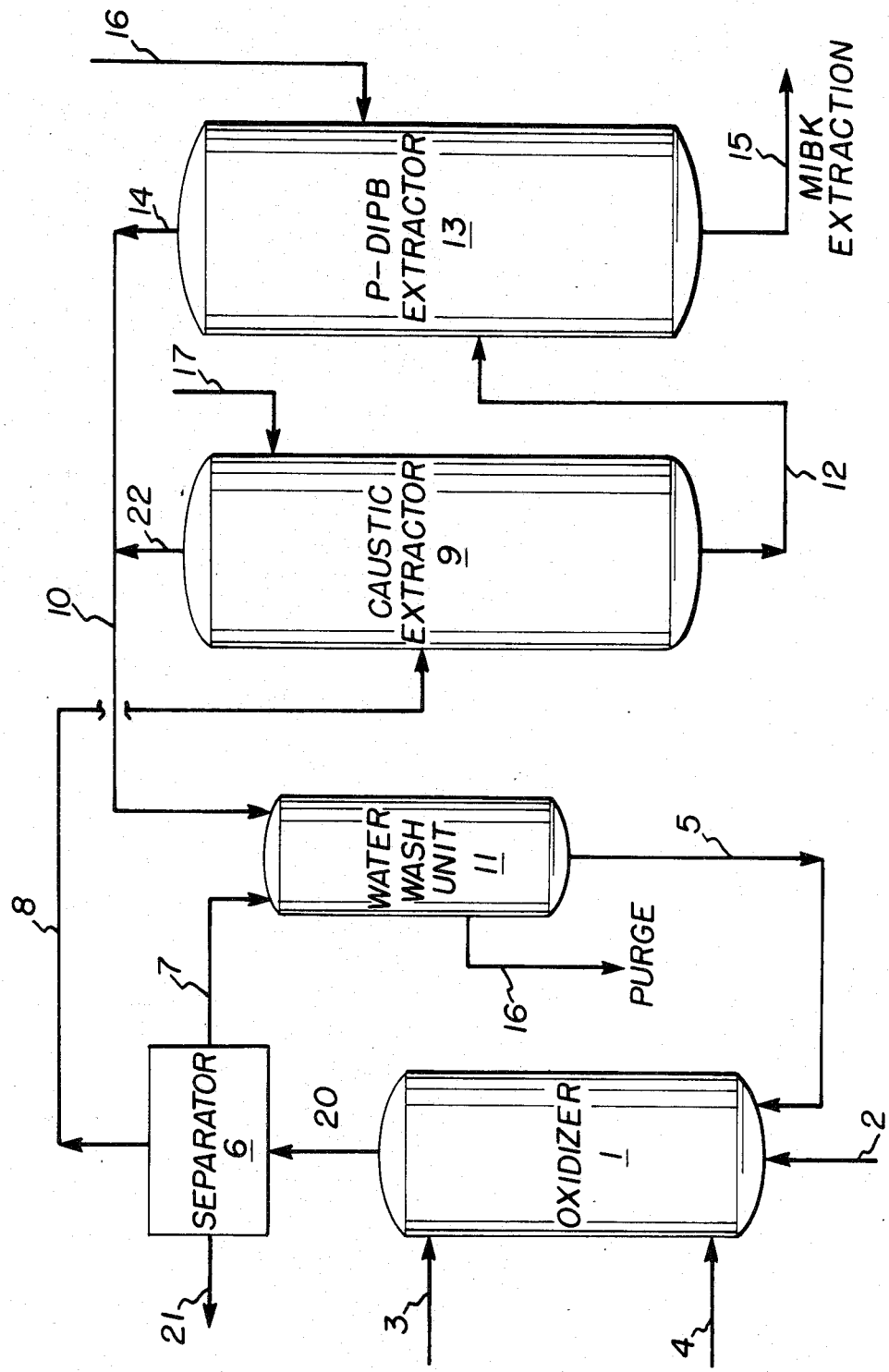

DIHYDRIC PHENOL RECOVERY PROCESS

BACKGROUND OF THE INVENTION

This invention relates to the production of dihydric phenols by the oxidation of dialkylbenzenes to dialkylbenzene dihydroperoxides and the acid-catalyzed rearrangement of the dihydroperoxides to the dihydric phenol.

It is known to oxidize meta and paradiisopropylbenzene to meta and para-diisopropylbenzene dihydroperoxide, and to rearrange the dihydroperoxide by acid cleavage (Hock splitting) resorcinol or hydroquinone. See for example Tanaka, et al U.S. Pat. No. 4,049,723, incorporated herein by reference for all purposes, the references disclosed therein, U.S. Pat. Nos. 4,053,520 and 3,968,171 and the paper by J. Ewers, H. W. Voges and G. Maleck entitled "Process for the Production of Hydroquinone", Erdoel Kohle Erdgas, Petrochem. Br. Chem., Vol. 28, No. 1, 1975, pp. 34+.

In the first step of the process, the dialkylbenzene is oxidized with oxygen to dialkylbenzene monohydroperoxide, e.g. para-diisopropyl-benzene monohydroperoxide, which is further oxidized to the dihydroperoxide. In this step the hydroperoxide groups are decomposed in various degrees which gives rise to several by-products including alcoholic and ketonic decomposition products and their further oxidation products. The main by-product is the hydroxyhydroperoxide which results from the oxidation of monocarbinol which itself results from the decomposition of the monohydroperoxide. Thus the process is optimized by choosing the reaction conditions to minimize the production of the hydroxyhydroperoxide. Elevation of the reaction temperature increases the production of the dihydroperoxide and the hydroxyhydroperoxide. However, the production of the hydroxyhydroperoxide increases at a greater rate with an increase in temperature. Thus the reaction is generally conducted at a temperature in the range from about 83° C. to about 87° C. in order to insure good dihydroperoxide yield and to minimize the reactor space required.

Using air as the oxidizing gas, generally the oxygen content of the exhaust gas from the reactor is kept below about 8% for safety reasons. This allows sufficient oxygen to be present in the reaction liquid such that the rate of oxidation is independent of the oxygen content in the liquid and thus is maximal. Formic acid is formed as a by-product of the reaction. Thus the oxidation is carried out in a weakly alkaline range. Low concentration sodium hydroxide, 0.3%, is added to the oxidizer with the oxidate to maintain the pH in the oxidizer from about 7.0 to about 7.5. The pH must be carefully controlled otherwise decomposition reactions are catalyzed increasing the concentration of by-products.

In the second step of the process, the aqueous caustic waste stream is separated from the organic oxidate stream after oxidation.

In the third step of the process, the organic oxidate is extracted with 4% by weight aqueous sodium hydroxide solution. In this step the dihydroperoxide and the hydroxyhydroperoxide enter the aqueous phase, together with other by-products, and unreacted dialkylbenzene, e.g. p-diisopropylbenzene, and monohydroperoxide is recovered for recycling to the oxidizer. Before recycling, however, entrained sodium hydroxide must be removed to insure adequate pH control in the oxidizer. Generally, this is accomplished by subjecting the recycle oxidate to the action of carbon dioxide and several subsequent water washes.

The fourth step of the process comprises transfer of the organic components in the 4% aqueous caustic solution into an organic solvent such as methyl isobutyl ketone and recycling the caustic solution.

The fifth step in the process comprises the acid-cataylzed splitting of the diisopropylbenzene dihydroperoxide, in the organic solvent, to the dihydric phenol and acetone.

The sixth step in the process comprises the separation and recovery of the dihydric phenol from the by-products and organic solvent.

The aqueous caustic waste stream separated from the oxidate in step two contains organic impurities and the desired intermediate, meta or paradiisopropylbenzene dihydroperoxide. These impurities result in a loss of product, and further processing is required to render the waste stream environmentally safe for disposal.

SUMMARY OF THE INVENTION

We have now found that the aqueous caustic waste stream can be utilized to wash the recycle oxidate in the third step of the process described above. In this manner, the caustic concentration is reduced to an acceptable level in the recycle oxidate, and dialkylbenzene dihydroperoxide in the aqueous caustic waste stream is recovered for recycling to the oxidizer.

Accordingly, it is an object of this invention to increase the yield of the dialkylbenzene dihydroperoxide in the re-cycle oxidate.

It is another object of this invention to utilize the aqueous caustic waste stream from the oxidizer to wash entrained caustic from the recycle oxidate.

These and other objects of this invention will become apparent to one skilled in the art upon reading this specification and the appended claims.

BRIEF DESCRIPTION OF THE DRAWING

The single FIGURE is a schematic flowsheet illustrating the process of this invention.

DESCRIPTION OF THE PREFERRED EMBODIMENTS

While the invention will be described with particular reference to the production and recovery of hydroquinone from the oxidation of a p-dialkylbenzene dihydroperoxide, it is to be understood that it is equally applicable to the production of other dihydric phenols, such as resorcinol, from the oxidation of meta-dialkylbenzenes such as m-diisopropylbenzene.

As indicated, methods are known for converting p-diisopropylbenzene to hydroquinone via oxidation to p-diisopropylbenzene dihydroperoxide, and acid-splitting this intermediate to hydroquinone. The process of the present invention can be utilized in any of these known processes which utilize the step of washing the recycle oxidate to decrease the concentration of caustic therein. See for example the paper by J. Ewers, et al referenced hereinbefore.

The process of this invention is practiced by flowing the aqueous waste stream from the oxidizer to the vessel containing the recycle oxidate, washing the recycle oxidate with the aqueous waste stream to decrease the entrained caustic concentration in the recycle oxidate and increase the concentration of p-diisopropylbenzene dihydroperoxide in the recycle oxidate, and thereafter separating the waste aqueous stream from the recycle oxidate.

The process will be illustrated by the following non-limiting example of the invention, the invention being limited only by the scope of the appended claims.

EXAMPLE 1

P-diisopropylbenzene was oxidized to p-diisopropylbenzene dihydroperoxide and various by-products with oxygen at a temperature of 105° to 110° C. The pH was maintained at 7 to 7.5 by the addition of a 0.3% by weight aqueous sodium hydroxide solution.

Referring now to the drawing, recycle oxidate and p-diisopropylbenzene from wash unit 11 via line 5, the aqueous caustic via line 4, and oxygen via line 2 were admitted into the bottom of the reactor (oxidizer) 1, the oxidate and exhaust gas exiting reactor via line 20 where it is sent to separator 6. Nitrogen via line 3 was added to the head space (top) of the reactor (oxidizer) to maintain the oxygen content of the exhaust gas from the reactor below about 8%. In separator 6, the oxidate is separated into an aqueous stream 7 and an organic stream 8, the organic stream 8 being fed to a caustic extractor 9 wherein the p-diisopropylbenzene dihydroperoxide, the p-hydroxyhydroperoxide, and certain impurities were extracted into the 4% aqueous caustic solution introduced into extractor 9 via line 17. Recycle oxidate from extractor 9 was fed to a water wash unit 11 via line 10. Simultaneously, the aqueous waste stream 7 from oxidizer 1 was admitted to wash unit 11. An aqueous stream from caustic extractor 9 and containing dihydroperoxide, monohydroperoxide and hydroxyhydroperoxide was fed via line 12 to extractor 13 where it was contacted with fresh p-diisopropylbenzene, introduced via 16, which extracted the valuable precursor p-diisopropylbenzene monohydroperoxide from the aqueous phase. The organic phase from extractor 13 was then fed to the wash unit 11 via line 10, the aqueous phase being fed via line 15 to a methyl isobutyl ketone extractor for further processing to hydroquinone.

In the wash unit 11, the caustic solution entrained in the recycle oxidate 22, from the caustic extractor 9 and in the organic phase 14 from the p-diisopropylbenzene (p-DIPB) extractor 13 is removed by the aqueous waste stream 7 from the oxidizer 1. Simultaneously, p-diisopropylbenzene dihydroperoxide present in the aqueous waste stream enters the organic phase which is recycled to the oxidizer via line 5, the aqueous phase from the wash unit 11 being purged from the system via line 16.

Using the process described above, sufficient caustic was removed from the recycle oxidate introduced into water wash unit 11 to permit good pH control of oxidizer 1. Additionally, at least 50% of the paradiisopropylbenzene dihydroperoxide was recovered from the waste water along with some of the waste solids present in the waste water.

EXAMPLE 2

The same procedure that was employed in Example 1 was utilized here except that m-diisopropylbenzene was used in lieu of p-diisopropylbenzene. In this procedure the temperature utilized was 110° C. and the caustic was 0.4% by weight aqueous sodium hydroxide solution. The result obtained was identical to Example 1 except that m-diisopropylbenzene dihydroperoxide was recovered.

The foregoing disclosure and description of the invention is illustrative and explanatory thereof, and various changes in the method steps may be made within the scope of the appended claims without departing from the invention.

We claim:

1. In a process for the manufacture of a dihydric phenol from a dialkylbenzene wherein, in an intermediate step, a dialkylbenzene is oxidized to the corresponding dialkylbenzene dihydroperoxide in an oxidizer with air in the presence of sufficient dilute aqueous sodium hydroxide to maintain the pH in the oxidizer in the range from about 7.0 to about 7.5, wherein an organic phase and an aqueous phase from the oxidizer are separated and the organic phase is extracted with an aqueous sodium hydroxide solution in a caustic extraction to extract the dihydroperoxide for further processing, and wherein the organic phase from the caustic extractor is recycled to the oxidizer, the improvement which comprises washing the organic phase from the caustic extractor with the aqueous phase from the oxidizer, feeding the organic phase from the wash unit to the oxidizer, and feeding the aqueous phase from the wash unit to a purge unit for disposal.

2. The process of claim 1 wherein said dialkylbenzene comprises a p-dialkylbenzene.

3. The process of claim 1 wherein said dialkylbenzene comprises a m-dialkylbenzene.

4. In a process for the manufacture of a dihydric phenol from a dialkylbenzene wherein, in an intermediate step, a dialkylbenzene is oxidized to the corresponding dihydroperoxide and various by-products in an oxidizer with air in the presence of sufficient dilute aqueous sodium hydroxide to maintain the pH in the range from about 7.0 to about 7.5, wherein an organic phase and an aqueous phase from the oxidizer are separated and the organic phase from the oxidizer is extracted with an aqueous caustic solution in a caustic extraction to extract the dihydroperoxide for further processing, and wherein the organic phase from the caustic extractor is recycled to the oxidizer, the improvement which comprises decreasing the concentration of entrained sodium hydroxide in the organic phase from the caustic extractor and increasing the concentration of dihydroperoxide recycled to the oxidizer by washing the organic phase from the caustic extractor with the aqueous phase from the oxidizer, separating the organic phase from the aqueous phase, and feeding the organic phase to the oxidizer.

5. The process of claim 4 wherein said dialkylbenzene comprises a p-dialkylbenzene.

6. The process of claim 4 wherein said dialkylbenzene comprises a m-dialkylbenzene.

7. In a process for the manufacture of a dihydric phenol from a dialkylbenzene wherein, in an intermediate step, a dialkylbenzene is oxidized to the corresponding dialkylbenzene dihydroperoxide in an oxidizer with oxygen in the presence of sufficient dilute aqueous sodium hydroxide to maintain the pH in the oxidizer in the range from about 7.0 to about 7.5, wherein an organic phase and an aqueous phase from the oxidizer are separated and the organic phase is extracted in a caustic extraction with an aqueous sodium hydroxide solution to extract the dihydroperoxide for further processing, and wherein the organic phase from the caustic extractor is recycled to the oxidizer, the improvement which comprises washing the organic phase from the caustic extractor with the aqueous phase from the oxidizer, feeding the organic phase from the wash unit to the oxidizer, and feeding the aqueous phase from the wash unit to a purge unit for disposal.

* * * * *